US012692559B2

(12) United States Patent
Kil et al.

(10) Patent No.: US 12,692,559 B2
(45) Date of Patent: Jul. 28, 2026

(54) PRIMER COMPOSITION FOR RECOMBINASE-POLYMERASE AMPLIFICATION REACTION FOR RAPID DIAGNOSIS OF ISRAELI ACUTE BEE PARALYSIS VIRUS AND USE THEREOF

(71) Applicant: Andong National University Industry-Academic Cooperation Foundation, Andong-si (KR)

(72) Inventors: Eui Joon Kil, Andong-si (KR); Chul Eui Jung, Seoul (KR); Man Cheol Son, Gyeongsangbuk-do (KR)

(73) Assignee: Andong National University Industry-Academic Cooperation Foundation, Andong-si (KR)

( * ) Notice: Subject to any disclaimer, the term of this patent is extended or adjusted under 35 U.S.C. 154(b) by 735 days.

(21) Appl. No.: 18/170,064

(22) Filed: Feb. 16, 2023

(65) Prior Publication Data

US 2023/0374613 A1        Nov. 23, 2023

(30) Foreign Application Priority Data

May 18, 2022        (KR) ........................ 10-2022-0060816

(51) Int. Cl.
| | |
|---|---|
| *C12Q 1/6844* | (2018.01) |
| *C12Q 1/686* | (2018.01) |
| *C12Q 1/6876* | (2018.01) |
| *C12Q 1/70* | (2006.01) |

(52) U.S. Cl.
CPC ............. *C12Q 1/70* (2013.01); *C12Q 1/6844* (2013.01)

(58) Field of Classification Search
None
See application file for complete search history.

(56) References Cited

U.S. PATENT DOCUMENTS 4,458,066 A        7/1984  Caruthers et al.

FOREIGN PATENT DOCUMENTS

| | | |
|---|---|---|
| EP | 0439182 B1 | 7/1991 |
| WO | 198801015 A1 | 12/1988 |
| WO | 199001069 A1 | 2/1990 |
| WO | 1990006995 A1 | 6/1990 |

OTHER PUBLICATIONS

Cagirgan et al. Development of a multiplex RT-PCR assay for the routine detection of seven RNA viruses in Apis mellifera. J Virol Methods. 2020; 281:113858.*
GenBank: KY465691.1. Israeli acute paralysis virus strain VN2 non-structural polyprotein and structural polyprotein genes, complete cds. Dated Aug. 13, 2017.*
Mayboroda et al. Multiplexed isothermal nucleic acid amplification. Anal Biochem . Mar. 15, 2018; 545:20-30.*
Euler et al. Recombinase polymerase amplification assay for rapid detection of Rift Valley fever virus. Journal of Clinical Virology, 54 (2012) 308-312.*
Marshall, O. Graphical Design of Primers with PerlPrimer. Methods Mol Biol. 2007; 402:403-14.*
S.L. Beaucage et al., "Deoxynucleoside phosphoramidites—A new class of key intermediates for deoxypolynucleotidesynthesis", Tetrahedron Letters, vol. 22, Issue 20, 1981, pp. 1859-1862.
S.A. Narang et al., "Improved phosphotriester method for the synthesis of gene fragments", Methods in Enzymology, vol. 68, 1979, pp. 90-98.

* cited by examiner

*Primary Examiner* — Nianxiang Zou
(74) *Attorney, Agent, or Firm* — You & IP, LLC

(57)        ABSTRACT

Proposed is a primer composition for a recombinase-polymerase amplification reaction for rapid diagnosis of Israeli acute paralysis virus and use thereof. A genomic RNA of Israeli acute paralysis virus (IAPV) is isolated from honey bees to analyze a nucleotide sequence of IAPV, and a primer pair capable of being detected by a recombinase-polymerase amplification method was prepared based on the IAPV RNA sequence. In addition, the optimal conditions of the prepared primer pair were confirmed, and it was confirmed that the genomic RNA of IAPV could be rapidly detected and diagnosed.

6 Claims, 6 Drawing Sheets

Specification includes a Sequence Listing.

- Agarose gel 1%

FIG. 3

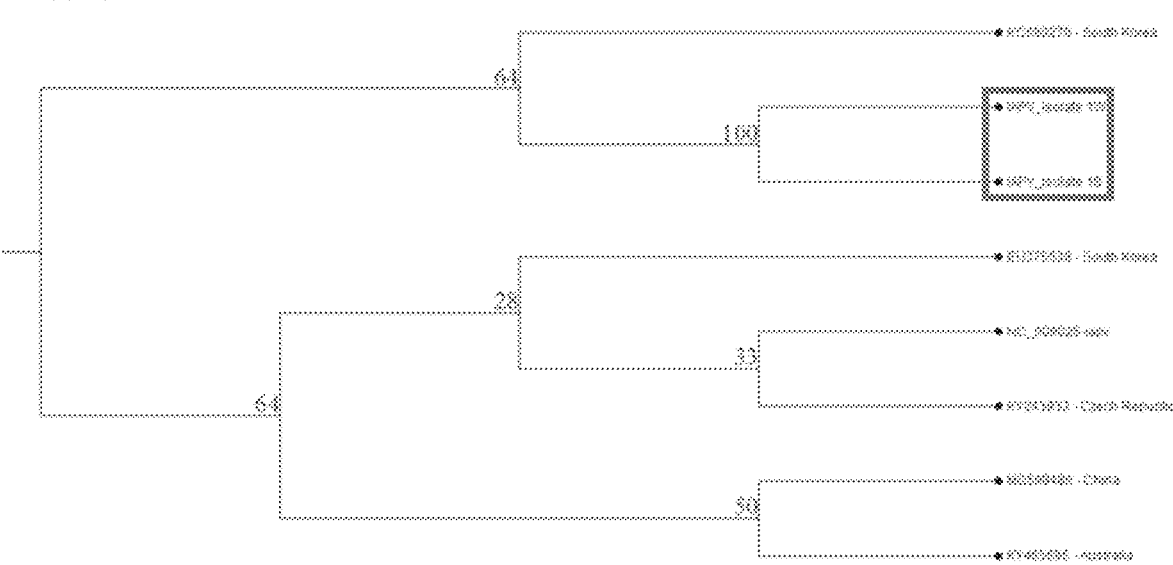

FIG. 4

| Primer pair | Sequence (5'-3') | Product size (bp) |
|---|---|---|
| Primer pair 1 | GCTAAACCTGGACTCAAGTTAGCTTCTAT | 191 |
| | GAAGGATCAACTTCTGGCATATCCATT | |
| Primer pair 2 | CTAAACCTGGACTCAAGTTAGCTTCT | 188 |
| | AGGATCAACTTCTGGCATATCCATT | |
| Primer pair 3 | AAACCTGGACTCAAGTTAGCTTCTA | 185 |
| | GGATCAACTTCTGGCATATCCATTT | |
| Primer pair 4 | TAAACCTGGACTCAAGTTAGCTTCT | 191 |
| | TTGAAGGATCAACTTCTGGCATATC | |
| Primer pair 5 | GCTTATATATTCCTGTGTCGGAGCAG | 100 |
| | GCGGGTTGTTTGGTGATTTTGTTAT | |

FIG. 5
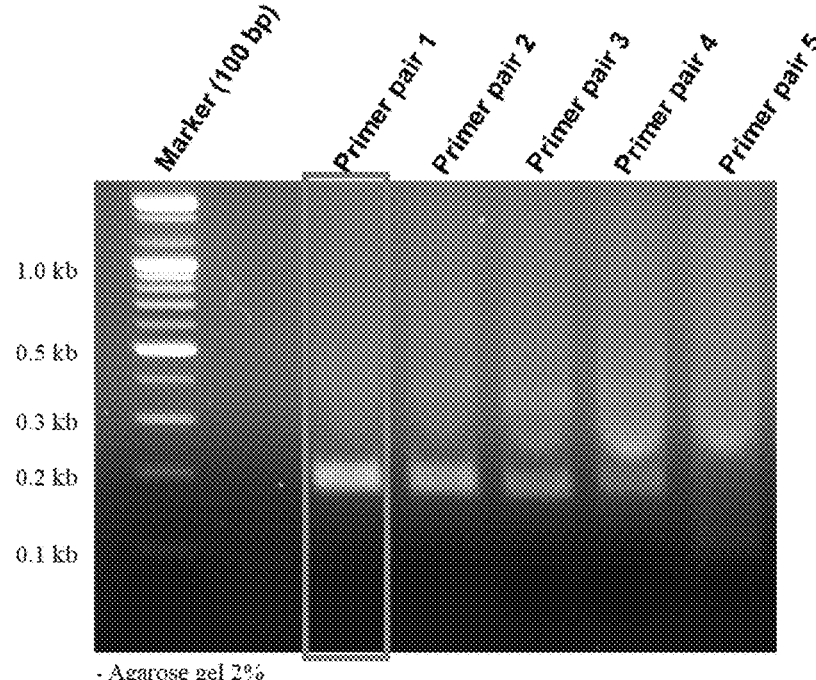
FIG. 6
A
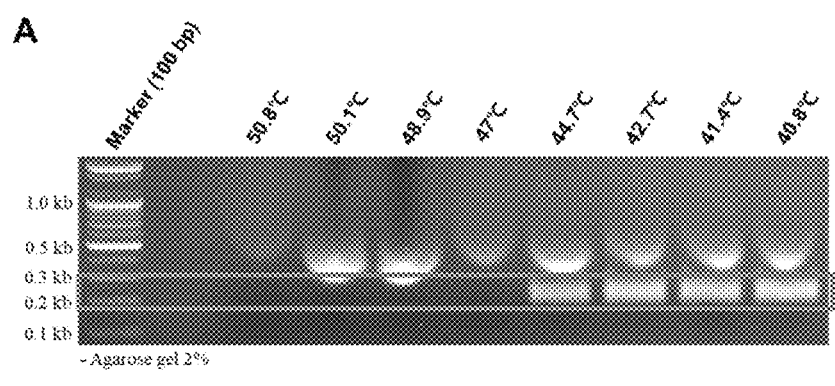
C
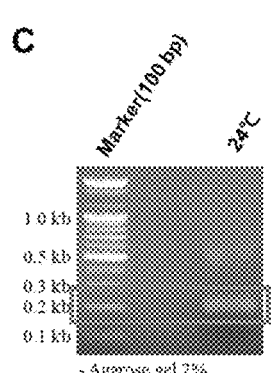
B
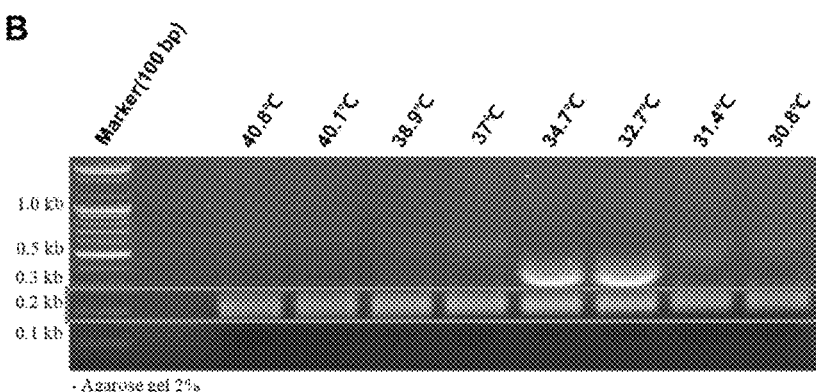

FIG. 7
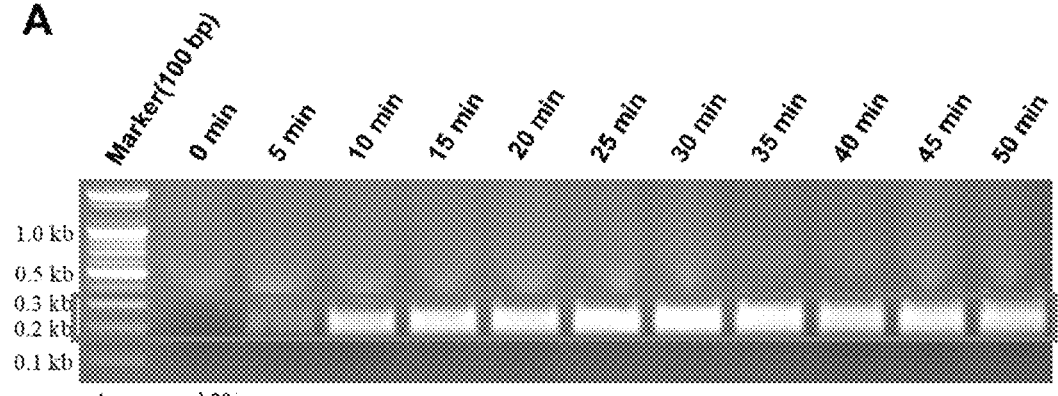
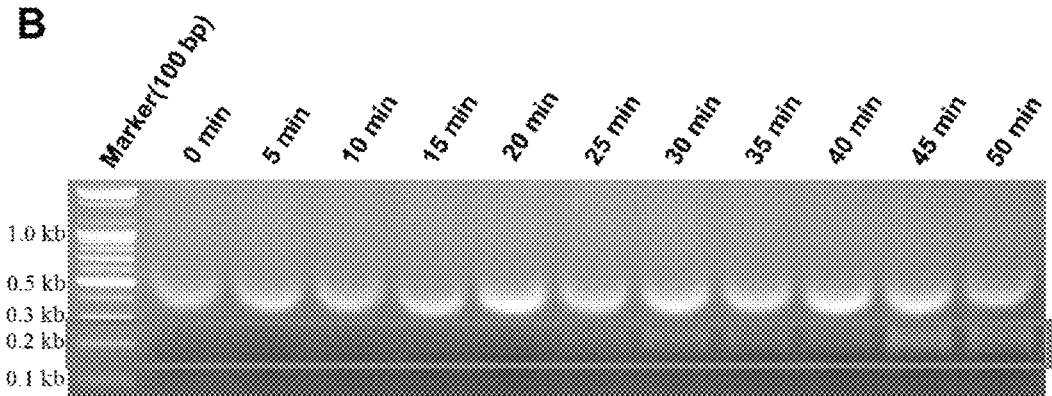
FIG. 8
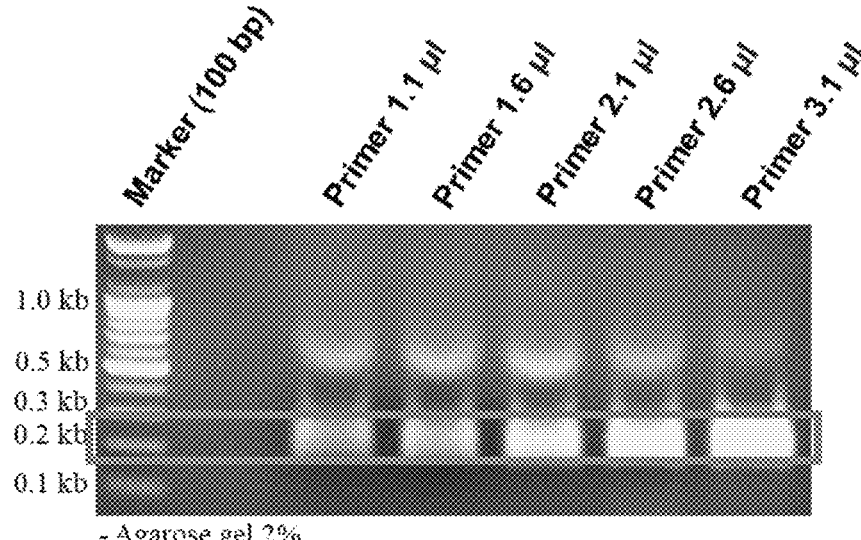

PRIMER COMPOSITION FOR RECOMBINASE-POLYMERASE AMPLIFICATION REACTION FOR RAPID DIAGNOSIS OF ISRAELI ACUTE BEE PARALYSIS VIRUS AND USE THEREOF

STATEMENT REGARDING GOVERNMENT SPONSORED RESEARCH

This invention was made with Korean government support under "Priority Research Institute Program" awarded by Ministry of Education of Republic of Korea and National Research Foundation of Korea.

REFERENCE TO A FOREIGN PRIORITY

The present application claims priority to Korean Patent Application No. 10-2022-0060816, filed May 18, 2022, the entire contents of which is incorporated herein for all purposes by this reference.

REFERENCE TO AN ELECTRONIC SEQUENCE LISTING

The contents of the electronic sequence listing (PANY-112-Sequence_Listing.xml; Size: 18,472 bytes; and Date of Creation: Feb. 16, 2023) is herein incorporated by reference in its entirety.

BACKGROUND OF THE INVENTION

Field of the Invention

The present disclosure relates to a primer composition for a recombinase-polymerase amplification reaction for rapid diagnosis of Israeli acute paralysis virus and the use thereof.

Description of the Related Art

Israeli acute paralysis is a disease that causes wing convulsions and paralysis of bees (*Apis mellifera*) and leads to death and is recognized as a disease closely related to the colony collapse disorder and is caused by the Israeli acute paralysis virus. Israeli acute paralysis virus is an ssRNA virus of the family Dicistroviridae and is known to be transmitted by *Varroa destructor* ingesting the body fluids of adults or larvae of infected bees. In order to detect such an Israeli acute paralysis virus, a commonly known diagnostic method is to extract the genetic material from suspected bees or *Varroa destructor* and then amplify and confirm a part of the gene required for diagnosis with a polymerase chain reaction (PCR). However, diagnosis using PCR takes at least 190 minutes from the extraction of nucleic acid to confirmation of amplification products during diagnosis, and it is difficult to detect and diagnose quickly because special equipment is required for each process during the extraction of genetic materials and PCR.

On the other hand, recombinase-polymerase amplification (RPA) is a method that can rapidly amplify specific DNA at isothermal and is applied to detect various pathogens by using the amplification of specific nucleotide sequences possessed by specific pathogens.

SUMMARY OF THE INVENTION

An objective of the present disclosure is to provide a primer set for detecting Israeli acute paralysis virus (IAPV)

including a primer pair selected from the group consisting of a primer pair of SEQ ID NO: 1 and SEQ ID NO: 2; a primer pair of SEQ ID NO: 3 and SEQ ID NO: 4; a primer pair of SEQ ID NO: 5 and SEQ ID NO: 6; a primer pair of SEQ ID NO: 7 and SEQ ID NO: 8; and a primer pair of SEQ ID NO: 9 and SEQ ID NO: 10.

Another objective of the present disclosure is to provide a composition for detecting the Israeli acute paralysis virus (IAPV) including the above primer set.

Still another objective of the present disclosure is to provide a kit for detecting Israeli acute paralysis virus (IAPV) including the above composition.

Still another objective of the present disclosure is to provide a method for detecting the Israeli acute paralysis virus (IAPV), the method including: extracting RNA from bee samples;

amplifying the extracted RNA using the kit; and
confirming the amplified product.

In order to achieve the above objective of the present disclosure, the present disclosure provides a primer set for detecting Israeli acute paralysis virus (IAPV) including a primer pair selected from the group consisting of a primer pair of SEQ ID NO: 1 and SEQ ID NO: 2; a primer pair of SEQ ID NO: 3 and SEQ ID NO: 4; a primer pair of SEQ ID NO: 5 and SEQ ID NO: 6; a primer pair of SEQ ID NO: 7 and SEQ ID NO: 8; and a primer pair of SEQ ID NO: 9 and SEQ ID NO: 10.

In addition, the present disclosure provides a composition for detecting the Israeli acute paralysis virus (IAPV) including the above primer set.

In addition, the present disclosure provides a kit for detecting Israeli acute paralysis virus (IAPV) including the above composition.

In addition, the present disclosure provides a method for detecting Israeli acute paralysis virus (IAPV), the method including: extracting RNA from bee specimens;

amplifying the extracted RNA using the kit; and
confirming the amplified product.

In the present disclosure, the RNA of the Israeli acute paralysis virus (IAPV) was isolated from honey bees, and a primer pair that can be detected by recombinase-polymerase amplification was prepared based on the IAPV genomic RNA sequence. In addition, after selecting a primer pair that shows the optimal diagnosis result among the prepared primer pairs, the optimum diagnosis condition using the above primer pair is confirmed. Through this, it was confirmed that RNA of IAPV can be rapidly detected and diagnosed, which can be useful in related industries.

BRIEF DESCRIPTION OF THE DRAWINGS

FIG. 3 is a diagram confirming the phylogenetic relationship between the previously reported IAPV and the IAPV detected in honey bee samples using the genomic RNA sequences of Israeli acute paralysis virus (IAPV);

FIG. 4 is a diagram confirming the information of the primer pairs 1-5 (SEQ ID NOS: 1-10) prepared for the recombinase-polymerase amplification (RPA) of the present disclosure;

FIG. 5 is a diagram confirming IAPV RNA detection with 5 primer pairs of the present disclosure;

FIG. 6 is a diagram confirming the optimal amplification temperature of primer pair 1 of the present disclosure (A: amplification at 40.8° C. to 50.8° C., B: amplification at 30.8° C. to 40.8° C., C: amplification at 24° C.);

FIG. 7 is a diagram confirming the optimal amplification time of primer pair 1 of the present disclosure (A: amplification at 37° C., B: amplification at 24° C.);

FIG. 8 is a diagram confirming the optimal amplification concentration of primer pair 1 of the present disclosure;

DESCRIPTION OF THE PREFERRED EMBODIMENTS

Figure 1:
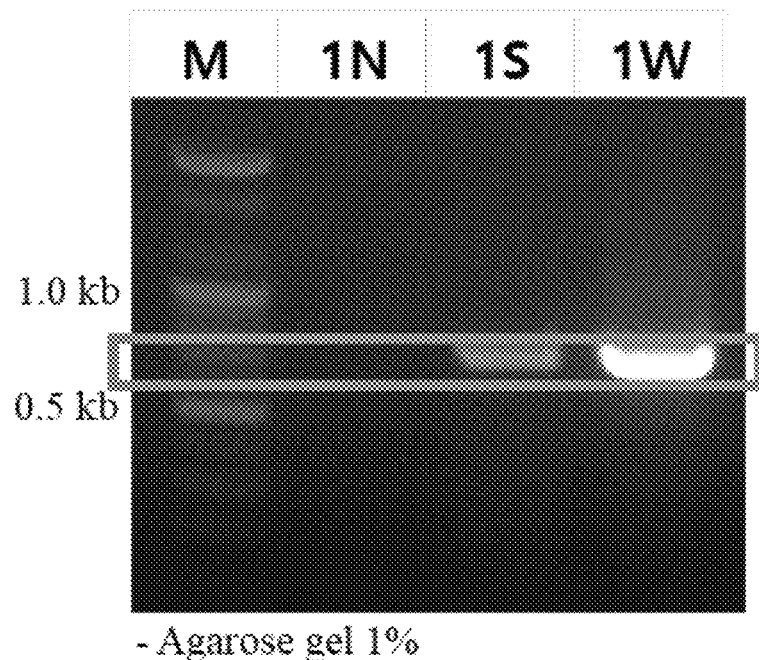
FIG. 1 is a diagram confirming the genomic RNA of Israeli acute paralysis virus (IAPV) in honey bee samples by RT-PCR.

Hereinbelow, exemplary embodiments of the present disclosure will be described in detail with reference to the accompanying drawings. In the following description, detailed descriptions of well-known technologies to those skilled in the art may be omitted. Furthermore, in describing this disclosure, if it is determined that a detailed description of a related known function or configuration may unnecessarily obscure the gist of this disclosure, the detailed description may be omitted. In addition, the terms used in this specification (terminology) are terms used to appropriately express preferred embodiments of the present disclosure, which may vary depending on the intention of the user or operator or the practice of the field to which this disclosure belongs.

Therefore, definitions of these terms should be made based on the contents throughout this specification. Throughout the specification, when a part "includes" a component, this means that other components may be further included rather than excluding the other components unless otherwise opposed.

The present disclosure provides a primer set for detecting Israeli acute paralysis virus (IAPV) including a primer pair selected from the group consisting of a primer pair of SEQ ID NO: 1 and SEQ ID NO: 2; a primer pair of SEQ ID NO: 3 and SEQ ID NO: 4; a primer pair of SEQ ID NO: 5 and SEQ ID NO: 6; a primer pair of SEQ ID NO: 7 and SEQ ID NO: 8; and a primer pair of SEQ ID NO: 9 and SEQ ID NO: 10.

The "Israeli acute paralysis virus (IAPV)" of this disclosure is a virus found during a study on chronic bee paralysis, closely related to acute honeybee paralysis and Kashmir honey bee disease, and is a virus in the Dicistroviridae family. It is known to be mainly related to bee mites, but research on this is insufficient, and it is known as a virus that greatly affects colony collapse disorder.

It is a highly toxic virus that kills pupae and adults within a few days, even with less than 100 virus particles (virion).

In the present disclosure, the term "primer" is a nucleic acid sequence with a short free 3' hydroxyl group. Primer refers to a short nucleic acid sequence that can form a base pair with a template of complementary nucleic acids and functions as a starting point for strand copying of nucleic acid templates. Primers can initiate DNA synthesis in the presence of a reagent for polymerization (i.e., DNA polymerase or reverse transcriptase) and four different nucleoside triphosphates in an appropriate buffer solution and temperature.

When designing the primers, various limitations such as A, G, C, T content ratio of the primer, prevention of dimer formation, prohibition of repeating the same base sequence three or more times, and other conditions such as the amount of template DNA, concentration of dNTP, concentration of $Mg^{2+}$, reaction temperature, reaction time, and the like should be appropriate under single PCR reaction conditions.

The above primers may incorporate additional features that do not change the basic properties. That is, nucleic acid sequences may be modified using a number of means known in the art. Examples of such modifications include methylation, capping, substitution of nucleotides with one or more homologues, and transformation of nucleotides into uncharged connections such as phosphonate, phosphotriester, phosphoramidate, or carbamate, or charged connections such as phosphorotioate or phosphorodithioate. In addition, nucleic acids may also have one or more additional covalently bonded residues such as proteins such as nucleases, toxins, antibodies, signaling peptides, and poly-L-lysine, and insertion agents such as acridine or psoralene, and chelating agents such as metals, radioactive metals, iron oxidizing metals, and alkylating agents.

In addition, the primer sequence of the present disclosure may be modified using a label capable of directly or indirectly providing a detectable signal. The primer may include a label that can be detected using spectroscopy, photochemistry, biochemistry, immunochemistry, or chemical means. Useful labels include 32P, fluorescent dyes, electron-dense reagents, enzymes (typically used in ELISA), biotin or hapten, and proteins available with anti-hemorrhagic or monoclonal antibodies.

The primer of the present disclosure may be chemically synthesized by using any other well-known method including a proper sequence cloning and restriction enzyme degradation, phosphotriester methods of Narang et al. (1979, Meth, Enzymol. 68:90-99), the diethylphosphoramidite method of Beaucage et al. (1981, Tetrahedron Lett. 22: 1859-1862), and direct chemical synthesis methods such as the solid support method in U.S. Pat. No. 4,458,066.

According to one embodiment of the present disclosure, the primer pair may be used for the recombinase-polymerase amplification (RPA) method.

The "recombinase-polymerase amplification (RPA)" of the present disclosure is a technology that can confirm DNA and RNA amplification based on PCR technology. Unlike the conventional PCR method, the RPA method can rapidly and accurately amplify a target sequence using a DNA-binding protein and a recombinase. Since amplification of the RPA method is possible even under isothermal conditions using mesophilic polymerases, viruses can be detected and diagnosed in a short time with an isothermal device without special equipment. However, since non-specific reactions often occur in the RPA method, it is important to prepare suitable primers to prevent this.

According to one embodiment of the present disclosure, the Israeli acute paralysis virus (IAPV) may include the nucleotide sequence of SEQ ID NO: 11.

In addition, the present disclosure provides a composition for detecting the Israeli acute paralysis virus (IAPV) including the above primer set.

The composition for detecting the virus of the present disclosure may include a primer or probe that specifically binds to IAPV, and the composition may further include a reaction amplification mixture. Reaction amplification mixtures refer to reagents needed to perform the amplification reaction, thermally stable DNA polymerase, deoxynucleotides, sterile water without nucleases, and solutions containing bivalent metal cations, etc. Preferably, a reaction amplification mixture may include a reaction buffer, deoxynucleotide, and DNA polymerase. A reporter, such as a fluorescent substance, may be labeled at the end of the probe.

According to one embodiment of the present disclosure, the composition may include 0.5 to 3.5 µl of primer pair selected from the group consisting of a primer pair of SEQ ID NO: 1 and SEQ ID NO: 2; a primer pair of SEQ ID NO: 3 and SEQ ID NO: 4; a primer pair of SEQ ID NO: 5 and SEQ ID NO: 6; a primer pair of SEQ ID NO: 7 and SEQ ID NO: 8; and a primer pair of SEQ ID NO: 9 and SEQ ID NO: 10, preferably 1.1 to 3.1 µl, more preferably 2.1 to 3.1 µl, but is not limited thereto.

According to one embodiment of the present disclosure, the composition may contain 0.5 to 4.0 µl of MgOAc, preferably 1.0 to 3.5 µl, more preferably 1.5 to 3.5 µl, but is not limited thereto.

According to one embodiment of the present disclosure, the composition may further include a DNA polymerase for a recombinase-polymerase amplification reaction, dNTPs, a reaction buffer, and distilled water.

In addition, the present disclosure provides a kit for detecting the Israeli acute paralysis virus (IAPV) including the above composition.

In addition, the present disclosure provides a method for detecting Israeli acute paralysis virus (IAPV), the method including: extracting RNA from bee specimens;

amplifying the extracted RNA using the kit; and confirming the amplified product.

The IAPV detection method of the present disclosure refers to a method for diagnosing IAPV infection containing the nucleotide sequence of SEQ ID NO: 11 in honey bee specimens. More specifically, the IAPV detection method may be a method capable of specifically detecting IAPV RNA by performing an amplification reaction using the primers for diagnosing IAPV of the present disclosure.

The "amplification reaction" refers to a reaction for amplifying a nucleic acid molecule and may include a recombinase-polymerase amplification (RPA), a polymerase chain reaction (PCR), and a reverse transcription-polymerase chain reaction (RT-PCR), ligase chain reaction (LCR), Gap-LCR (WO 90/01069), repair chain reaction (EP 439,182), transcription-mediated amplification (TMA: WO88/10315), self-sustained sequence replication (WO90/06995), selective amplification of target polynucleotide sequences, consensus sequence primed polymerase chain reaction (CPPCR), arbitrarily primed polymerase chain reaction (AP-PCR), nucleic acid sequence-based amplification (NASBA), strand displacement amplification, and loop-mediated isothermal amplification (LAMP), but is not limited thereto.

According to one embodiment of the present disclosure, the amplification may be amplified by recombinase polymerase amplification (RPA).

According to one embodiment of the present disclosure, the recombinase-polymerase amplification method may be performed at a temperature condition in a range of 20° C. to 50° C., preferably 20° C. to 45° C., but is not limited thereto.

According to one embodiment of the present disclosure, the recombinase-polymerase amplification method may be performed for 5 to 50 minutes, preferably 25 to 45 minutes, but is not limited thereto.

According to one embodiment of the present disclosure, the identification of the amplification product may be confirmed by a method selected from the group consisting of a DNA chip, gel electrophoresis, radiation measurement, fluorescence measurement, and phosphorescence measurement, preferably gel electrophoresis method, but is not limited thereto. Gel electrophoresis may use agarose gel electrophoresis or acrylamide gel electrophoresis, depending on the size of the amplification product.

Hereinbelow, the embodiments of the present disclosure will be described in more detail with reference to examples. These examples are merely for explaining the present disclosure in more detail, and it will be apparent to those skilled in the art that the scope of the present disclosure is not limited to these examples.

<Example 1> Viral RNA Extraction and Confirmation from Honey Bee Samples

<1-1 Viral RNA Extraction>

It was confirmed whether the Israeli acute paralysis virus (IAPV) could be detected in bees in Korea. Specifically, bees were provided from Insect Ecology-Pollinator Laboratory, Andong National University located in Gyeongdong-ro, Andong-si, Gyeongsangbuk-do. The provided bee samples were divided into strong and weak honey bee groups, and then 0.2 g (2 animals) of the bee sample was finely ground in a mortar and added to a 1.5 ml tube. Thereafter, after extracting Viral Gene-spin™ RNA using Viral DNA/RNA Extraction (Intronbio), RT-PCR was performed using SuPrimeScript RT-PCR Premix (2×) (GENETBIO), and PCR products were confirmed using electrophoresis. Primer pairs used for PCR analysis are shown in Table 1 below.

TABLE 1

| Primer | Sequence (5'-3') | Product size (bp) |
|---|---|---|
| F | GATTTGAGAGATGTAT TTCCTTCTGCGG (SEQ ID NO: 12) | 725 |
| R | ACACTTGCGTTGGTC CTGAATGTTAATGG (SEQ ID NO: 13) | |

As a result, as shown in FIG. 1, an electrophoresis product having the desired size was confirmed.

<1-2 Viral RNA Analysis>

The nucleotide sequence of the PCR product obtained in Example 1-1 was analyzed. Specifically, after analyzing the nucleotide sequence of the obtained PCR product, CLC Sequencing Viewer 8 was used to check whether the sequence was consistent with the sequence of existing IAPVs registered in NCBI (KC690270, MG599488, NC_009025, KY243933, KY465695, and EU375538). The detected IAPV RNA sequence information is shown in Table 2 below.

TABLE 2

| Sample name | Sequence |
|---|---|
| IAPV | GATTTGAGAGATGTATTTCC<br>TTCTGCGGTTGACGAAATGG<br>CCATAGGGTATGTTTGCGGC<br>AATCCAGCCGTGAAACATGT<br>TCTTACTTGGAAGACGACTG<br>ACGCAATTCAGAAACCAATA<br>GCAAACGGAGATGATTGGGG<br>TGGAGTTATACCAGTGGGAA<br>TGCCTTGTTATNCTAAATCT<br>ATTAGAACTACAAGTATTTC<br>AGAAACGGAAAATCGTGAAA<br>CTGAAGTCATAGATGCCGCT<br>CCATGTGAATATGTTGCTAA<br>CATGTTCTCGTATTGGCGTG<br>CAACTATGTGTTATAGGATT<br>ACTGTGGTGAAGACAGCTTT<br>TCATACTGGCAGACTTGAGA<br>TTTTCTTTGAACCGGGAGTG<br>ATACCCGTCAAACCCACTGT<br>TAATAATATTGGGCCCGATC<br>AGGATCAACTCACAGGAGCG<br>GTGGCTCCTTCCGATAATAA<br>CTATAAGTACATTTTGGACC<br>TAACCAATGATACAGAAGTT<br>ACAATACGTGTTCCTTTTGT<br>TTCAAATAAGATGTTCCTTA<br>AGACTGCTGGAATCTATGGT<br>GCTAATAGTGAAAATAACTG<br>GAACTTTCATGAGTCCTTTA<br>GTGGATTCTTATGTATAAGA<br>CCAGTCACTAAATTGATGGC<br>TCCTGATACTGTGTCTGACA<br>ATGTATCTATAGTTGTTTGG<br>AAGTGGGCAGAAGATGTNGT<br>AGTAGTAGAACCAAAACCAT<br>TAACATTCAGGACCAACGCA<br>AGTGT (SEQ ID NO: 11) |

Figure 2:
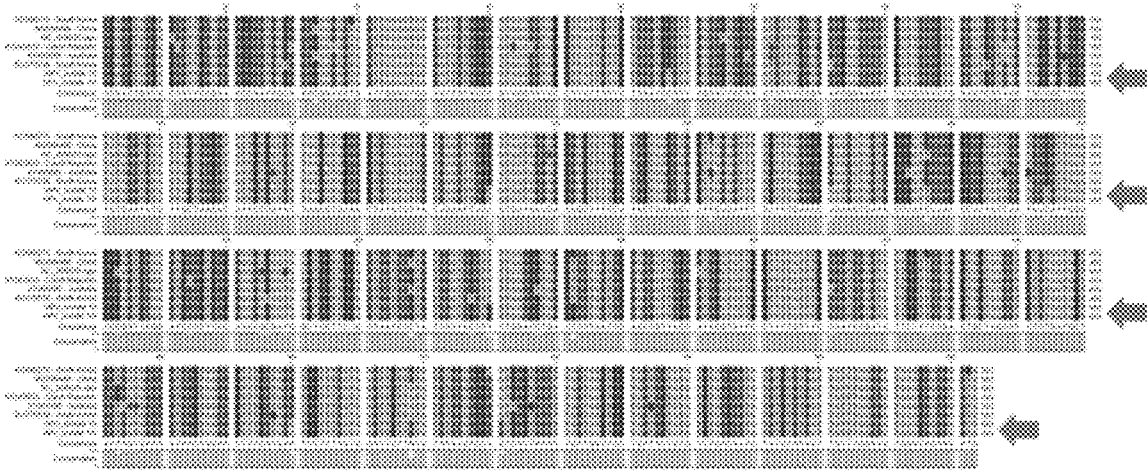
FIG. 2 is a diagram confirming the sequence homogeneity between the genomic RNA sequence of Israeli acute paralysis virus (IAPV) detected in honey bee samples (SEQ ID NO: 11) and the previously reported sequence of IAPV by multiple alignment.

As a result, a sequence with high homogeneity to the existing IAPV was confirmed in the honey bee sample of the present disclosure, and it was confirmed that the sequence was also highly homologous to the IAPV sequence previously reported in Korea (FIGS. 2 and 3).

<Example 2> Optimization of Recombinase-Polymerase Amplification Method for IAPV Detection <2-1> Primer Design for IAPV Detection Primers for detecting IAPV were prepared using the recombinase-polymerase amplification (RPA) method of the present disclosure. Specifically, based on the IAPV nucleotide sequence analyzed in Example 1 and the previously reported IAPV nucleotide sequence, Primer BLAST was performed to prepare 5 primer pairs. Thereafter, a primer pair suitable for RPA diagnosis of IAPV was identified from the prepared primer pair, and an appropriate primer pair was selected by performing RPA analysis. Information on the prepared 5 pairs of primers is shown in FIG. 4 and Table 3 below.

TABLE 3

| Primer pair | Sequence | Product size (bp) |
|---|---|---|
| Primer pair 1 | GCTAAACCTGGACTCAAGTTAGCTT<br>CTAT<br>(SEQ ID NO: 1) | 191 |

TABLE 3-continued

| Primer pair | Sequence | Product size (bp) |
|---|---|---|
| | GAAGGATCAACTTCTGGCATATCCA<br>TT<br>(SEQ ID NO: 2) | |
| Primer pair 2 | CTAAACCTGGACTCAAGTTAGCTTCT<br>(SEQ ID NO: 3)<br>AGGATCAACTTCTGGCATATCCATT<br>(SEQ ID NO: 4) | 188 |
| Primer pair 3 | AAACCTGGACTCAAGTTAGCTTCTA<br>(SEQ ID NO: 5)<br>GGATCAACTTCTGGCATATCCATTT<br>(SEQ ID NO: 6) | 185 |
| Primer pair 4 | TAAACCTGGACTCAAGTTAGCTTCT<br>(SEQ ID NO: 7)<br>TTGAAGGATCAACTTCTGGCATATC<br>(SEQ ID NO: 8) | 191 |
| Primer pair 5 | GCTTATATATTCCTGTGTCGGAGCAG<br>(SEQ ID NO: 9)<br>GCGGGTTGTTTGGTGATTTTGTTAT<br>(SEQ ID NO: 10) | 100 |

As a result, as shown in FIG. 5, it was confirmed that primer pair 1 among the above primer pairs was a primer pair suitable for RPA analysis. In fact, as a result of RPA analysis, it was confirmed that the band of the amplified product was the most pronounced in primer pair 1.

<2-2> Optimization of RPA Conditions (Check Temperature Conditions)

In order to optimize the isothermal maintenance condition, which is important in RPA analysis, the optimal RPA analysis temperature was identified. Specifically, IAPV was detected using the primers of Example 2-1 at various temperature conditions in a range of 30.8° C. to 50.8° C. In addition, RPA was additionally performed at 24° C., which is generally recognized as room temperature.

As a result, as shown in FIGS. 6A and 6B, it was confirmed that no amplification product was detected at a temperature exceeding 44.7° C. under the temperature conditions in a range of 30.8° C. to 50.8° C. In addition, it was confirmed that amplification products begin to be detected at 24° C. (FIG. 6C), and that the RPA of this disclosure can detect IAPV under a temperature condition in a range of 30.8° C. to 44.7° C., and that IAPV can be detected at room temperature.

<2-2> Optimization of RPA Conditions (Check Time Conditions)

In order to optimize the isothermal maintenance condition, which is important in RPA analysis, the optimal isothermal maintenance time was identified. Specifically, IAPV was detected using RPA for 0 to 50 minutes at 37° C. In addition, in order to confirm the optimal time condition at room temperature, IAPV was detected using RPA for 0 to 50 minutes, even at 24° C.

As a result, as shown in FIG. 7A, the amplification product was confirmed from 10 minutes of reaction at 37° C. and was most clearly observed at 25 minutes. In addition, it was confirmed that the amplification product was most clearly observed at 45 minutes of reaction at 24° C. (FIG. 7B).

In order to optimize the RPA analysis, the IAPV detection effect according to the amount of primer added was confirmed. Specifically, IAPV was detected by RPA by adding the primer of Example 2-1 at a concentration difference of 0.5 μl from 1.1 to 3.1 μl.

As a result, as shown in FIG. 8, as the amount of primer added increased, the amplification product was observed more clearly, but the amplified product band also increased in size so that the exact size of the amplified product could not be identified, and when 2.1 μl of primer was added, it was easy to identify the sharpness and size of the amplified product.

<2-2> Optimization of RPA Conditions (Checking the Optimal Amount of MgOAc Added)

MgOAc is the most important reactant in RPA analysis, and the efficiency of IAPV analysis according to the amount of MgOAc added was confirmed. Specifically, RPA for IAPV detection was performed by adding MgOAc at a concentration difference of 0.5 μl from 1.0 μl to 3.5 μl.

Figure 9:
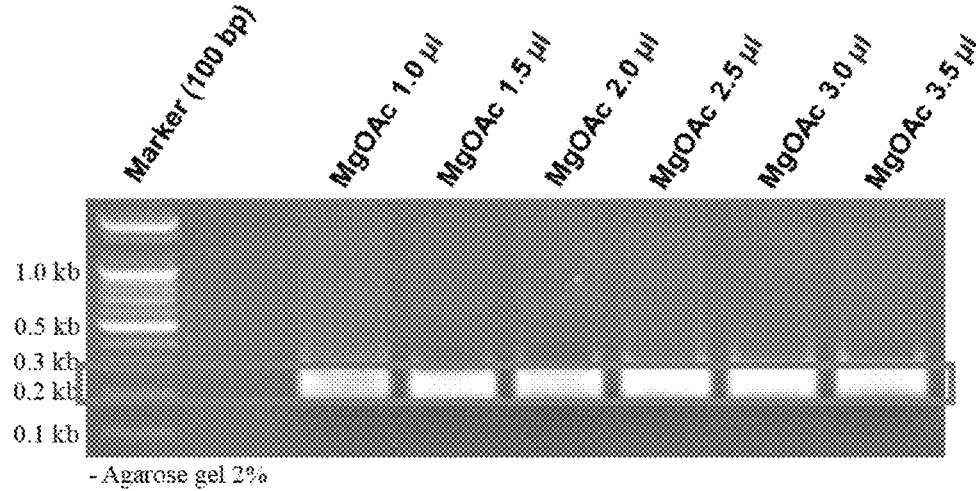
FIG. 9 is a diagram confirming the optimal concentration of MgOAc in the amplification reaction of primer pair 1 of the present disclosure.

As a result, as shown in FIG. 9, there was no significant difference in the detection of amplification products according to the amount of MgOAc added.

<Example 3> Optimization of RNA Extraction to Reduce IAPV Diagnosis Time

For rapid detection and diagnosis of IAPV, Quick-Extract™ DNA Extraction Solution (LGC Biosearch Technologies) was used to shorten RNA extraction time. Specifically, bee samples were ground and prepared, diluted in sterilized distilled water, mixed with Extraction Solution at a ratio of 1:1, and reacted at 95° C. for 5 minutes. After the end of the culture, the supernatant was obtained. Thereafter, the obtained supernatant was amplified using Real-time PCR, RT-PCR, and RPA, and it was confirmed whether the Quick-Extract™ DNA Extraction Solution could be used for IAPV detection.

Figure 10:
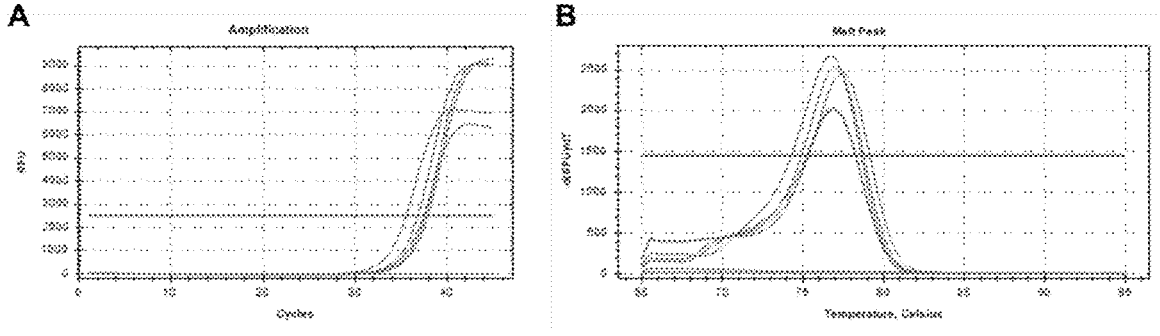
FIG. 10 is a diagram confirming the effect of real-time PCR according to the use of the Quick Extract kit when extracting IAPV RNA (A: check amplification, B: melt peak check)

RNA obtained by Quick-Extract™ DNA Extraction Solution was amplified by real-time PCR as a template. As a result of the analysis, it was confirmed that an amplification product of a desired size (FIG. 10A) and an amplification product constituting a configuration (FIG. 10B) was detected.

Figure 11:
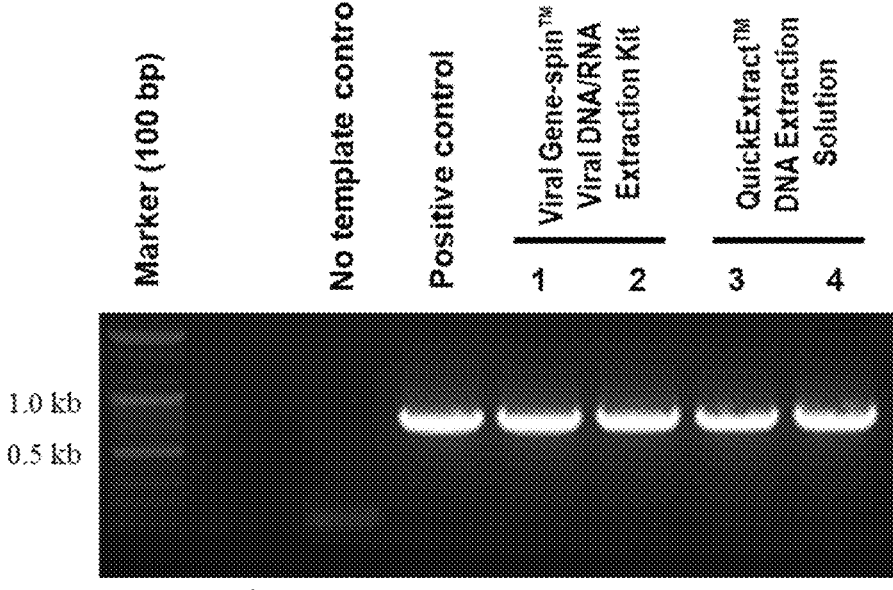
FIG. 11 is a diagram confirming the effect of RT-PCR according to the use of the Quick Extract kit when extracting IAPV RNA.
Figure 12:
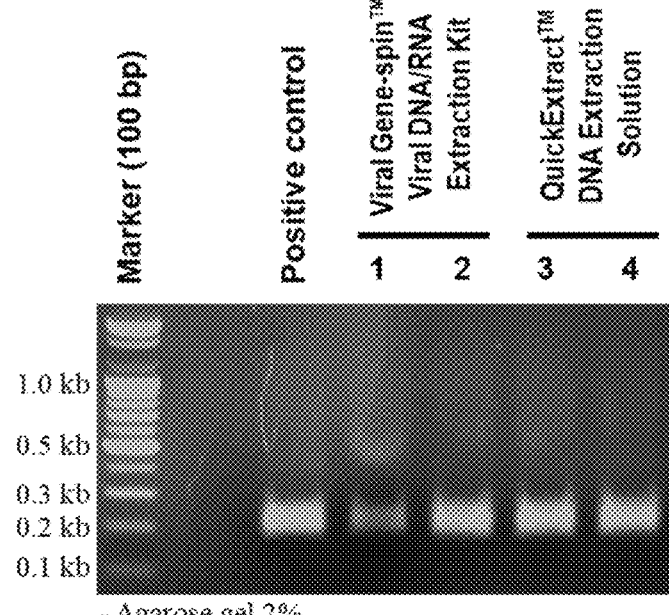
FIG. 12 is a diagram confirming the results by performing RPA after extracting RNA from various IAPV-infected samples using the Quick Extract kit.

In addition, an amplification product of the desired size was detected in RT-PCR (FIG. 11), and it was confirmed that amplification was performed equally well in RPA (FIG. 12). Based on the above results, it was confirmed that RNA extraction and diagnosis were performed accurately even when using the Quick-Extract™ DNA Extraction Solution, which can quickly extract RNA, and it was confirmed that the present disclosure can also be applied to RPA detection of IAPV.

Therefore, in the present disclosure, the RNA of Israeli acute paralysis virus (IAPV) was isolated from bees to analyze the nucleotide sequence of IAPV, and based on the IAPV RNA sequence, a primer pair that can be detected by recombinase-polymerase amplification was prepared. In addition, the optimal conditions of the prepared primer pair were confirmed, and it was confirmed that the RNA of IAPV could be rapidly detected and diagnosed.

---

What is claimed is:

1. A primer set for detecting Israeli acute paralysis virus (IAPV), the primer set consisting of a forward primer consisting of the nucleotide sequence of SEQ ID NO: 1 and a reverse primer consisting of the nucleotide sequence of SEQ ID NO: 2, wherein the primer set generates an amplification product having a length of 191 base pairs from a target nucleic acid comprising the nucleotide sequence of SEQ ID NO: 11 in a recombinase polymerase amplification reaction performed at a temperature of 24° C. for 45 minutes.

2. A composition for detecting Israeli acute paralysis virus (IAPV), the composition comprising:

a primer set consisting of a forward primer consisting of the nucleotide sequence of SEQ ID NO: 1 and a reverse primer consisting of the nucleotide sequence of SEQ ID NO: 2, wherein the primer set generates an amplification product having a length of 191 base pairs from a target nucleic acid comprising the nucleotide sequence of SEQ ID NO: 11 in a recombinase polymerase amplification reaction performed at a temperature of 24° C. for 45 minutes.

3. The composition of claim 2, comprising 0.5 to 3.5 µl of the primer set.

4. The composition of claim 2, comprising 0.5 to 4.0 µl of MgOAc.

5. The composition of claim 2, further comprising a DNA polymerase for a recombinase-polymerase amplification reaction, dNTPs, a reaction buffer, and distilled water.

6. A method for detecting Israeli acute paralysis virus (IAPV), the method comprising:

providing a bee specimen;

grinding the bee specimen to form a ground bee specimen;

diluting the ground bee specimen in sterilized distilled water to form a diluted bee specimen;

mixing the diluted bee specimen with a DNA extraction solution at a volume ratio of 1:1 to form an extraction mixture;

heating the extraction mixture at 95° C. for 5 minutes to form a heated mixture;

separating a supernatant from the heated mixture;

amplifying Israeli acute paralysis virus RNA contained in the supernatant in a recombinase polymerase amplification reaction performed at 24° C. for 45 minutes using a forward primer consisting of the nucleotide sequence of SEQ ID NO: 1 and a reverse primer consisting of the nucleotide sequence of SEQ ID NO: 2 to generate an amplification product having a length of 191 base pairs; and confirming the amplification product by gel electrophoresis.

*    *    *    *    *

```
                         SEQUENCE LISTING

Sequence total quantity: 13
SEQ ID NO: 1            moltype = DNA  length = 29
FEATURE                 Location/Qualifiers
misc_feature            1..29
                        note = IAPV RPA primer pair 1-F
source                  1..29
                        mol_type = other DNA
                        organism = synthetic construct
SEQUENCE: 1
gctaaacctg gactcaagtt agcttctat                                    29

SEQ ID NO: 2            moltype = DNA  length = 27
FEATURE                 Location/Qualifiers
misc_feature            1..27
                        note = IAPV RPA primer pair 1-R
source                  1..27
                        mol_type = other DNA
                        organism = synthetic construct
SEQUENCE: 2
gaaggatcaa cttctggcat atccatt                                      27

SEQ ID NO: 3            moltype = DNA  length = 26
FEATURE                 Location/Qualifiers
misc_feature            1..26
                        note = IAPV RPA primer pair 2-F
source                  1..26
                        mol_type = other DNA
                        organism = synthetic construct
SEQUENCE: 3
ctaaacctgg actcaagtta gcttct                                       26

SEQ ID NO: 4            moltype = DNA  length = 25
FEATURE                 Location/Qualifiers
misc_feature            1..25
                        note = IAPV RPA primer pair 2-R
source                  1..25
                        mol_type = other DNA
                        organism = synthetic construct
SEQUENCE: 4
aggatcaact tctggcatat ccatt                                        25
```

-continued

```
SEQ ID NO: 5            moltype = DNA   length = 25
FEATURE                 Location/Qualifiers
misc_feature            1..25
                        note = IAPV RPA primer pair 3-F
source                  1..25
                        mol_type = other DNA
                        organism = synthetic construct
SEQUENCE: 5
aaacctggac tcaagttagc ttcta                                      25

SEQ ID NO: 6            moltype = DNA   length = 25
FEATURE                 Location/Qualifiers
misc_feature            1..25
                        note = IAPV RPA primer pair 3-R
source                  1..25
                        mol_type = other DNA
                        organism = synthetic construct
SEQUENCE: 6
ggatcaactt ctggcatatc cattt                                      25

SEQ ID NO: 7            moltype = DNA   length = 25
FEATURE                 Location/Qualifiers
misc_feature            1..25
                        note = IAPV RPA primer pair 4-F
source                  1..25
                        mol_type = other DNA
                        organism = synthetic construct
SEQUENCE: 7
taaacctgga ctcaagttag cttct                                      25

SEQ ID NO: 8            moltype = DNA   length = 25
FEATURE                 Location/Qualifiers
misc_feature            1..25
                        note = IAPV RPA primer pair 4-R
source                  1..25
                        mol_type = other DNA
                        organism = synthetic construct
SEQUENCE: 8
ttgaaggatc aacttctggc atatc                                      25

SEQ ID NO: 9            moltype = DNA   length = 26
FEATURE                 Location/Qualifiers
misc_feature            1..26
                        note = IAPV RPA primer pair 5-F
source                  1..26
                        mol_type = other DNA
                        organism = synthetic construct
SEQUENCE: 9
gcttatatat tcctgtgtcg gagcag                                     26

SEQ ID NO: 10           moltype = DNA   length = 25
FEATURE                 Location/Qualifiers
misc_feature            1..25
                        note = IAPV RPA primer pair 5-R
source                  1..25
                        mol_type = other DNA
                        organism = synthetic construct
SEQUENCE: 10
gcgggttgtt tggtgatttt gttat                                      25

SEQ ID NO: 11           moltype = DNA   length = 725
FEATURE                 Location/Qualifiers
misc_feature            1..725
                        note = IAPV RNA sequence
source                  1..725
                        mol_type = other DNA
                        organism = synthetic construct
SEQUENCE: 11
gatttgagag atgtatttcc ttctgcggtt gacgaaatgg ccatagggta tgtttgcggc  60
aatccagccg tgaaacatgt tcttacttgg aagacgactg acgcaattca gaaaccaata  120
gcaaacggag atgattgggg tggagttata ccagtgggaa tgccttgtta tnctaaatct  180
attagaacta caagtatttc agaaacggaa aatcgtgaaa ctgaagtcat agatgccgct  240
ccatgtgaat atgttgctaa catgttctcg tattggcgtg caactatgtg ttataggatt  300
actgtggtga agacagcttt tcatactggc agacttgaga ttttctttga accgggagtg  360
atacccgtca aacccactgt taataatatt gggcccgatc aggatcaact cacaggagcg  420
gtggctcctt ccgataataa ctataagtac attttggacc taaccaatga tacagaagtt  480
acaatacgtg ttcctttgt ttcaaataag atgttcctta agactgctgg aatctatggt  540
gctaatagtg aaaataactg gaactttcat gagtcctta gtggattctt atgtataaga  600
ccagtcacta aattgatggc tcctgatact gtgtctgaca atgtatctat agttgtttgg  660
```

-continued

```
aagtgggcag aagatgtngt agtagtagaa ccaaaaccat taacattcag gaccaacgca   720
agtgt                                                              725

SEQ ID NO: 12          moltype = DNA  length = 28
FEATURE                Location/Qualifiers
misc_feature           1..28
                       note = IAPV RT-PCR primer F
source                 1..28
                       mol_type = other DNA
                       organism = synthetic construct
SEQUENCE: 12
gatttgagag atgtatttcc ttctgcgg                                      28

SEQ ID NO: 13          moltype = DNA  length = 29
FEATURE                Location/Qualifiers
misc_feature           1..29
                       note = IAPV RT-PCR primer R
source                 1..29
                       mol_type = other DNA
                       organism = synthetic construct
SEQUENCE: 13
acacttgcgt tggtcctgaa tgttaatgg                                     29
```